US009653271B2

(12) United States Patent
Shion et al.

(10) Patent No.: US 9,653,271 B2
(45) Date of Patent: May 16, 2017

(54) METHODS AND APPARATUS FOR PERFORMING MASS SPECTROMETRY

(71) Applicant: Waters Technologies Corporation, Milford, MA (US)

(72) Inventors: Henry Y. Shion, Andover, MA (US); Giorgis Mezengie Isaac, Marlborough, MA (US); Alan Millar, Southborough, MA (US); Tim Riley, Ann Arbor, MI (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/405,544

(22) PCT Filed: Jun. 7, 2013

(86) PCT No.: PCT/US2013/044649
§ 371 (c)(1),
(2) Date: Dec. 4, 2014

(87) PCT Pub. No.: WO2013/184995
PCT Pub. Date: Dec. 12, 2013

(65) Prior Publication Data
US 2015/0170893 A1 Jun. 18, 2015

Related U.S. Application Data

(60) Provisional application No. 61/693,890, filed on Aug. 28, 2012, provisional application No. 61/656,647, filed on Jun. 7, 2012.

(51) Int. Cl.
*H01J 49/00* (2006.01)
*G01N 27/62* (2006.01)
*H01J 49/16* (2006.01)

(52) U.S. Cl.
CPC ........ *H01J 49/0031* (2013.01); *G01N 27/622* (2013.01); *H01J 49/0045* (2013.01); *H01J 49/164* (2013.01); *H01J 49/165* (2013.01)

(58) Field of Classification Search
USPC ................ 250/281, 282, 283, 286, 287, 288
See application file for complete search history.

(56) References Cited

U.S. PATENT DOCUMENTS

| 7,429,729 B2 | 9/2008 | Schultz et al. | |
|---|---|---|---|
| 7,687,772 B2 | 3/2010 | Shiea | |
| 7,860,685 B2 | 12/2010 | Ho et al. | |
| 7,868,421 B2 | 1/2011 | Won et al. | |
| 8,022,359 B2 | 9/2011 | Michelmann | |
| 8,178,834 B2 | 5/2012 | Gorenstein et al. | |
| 2008/0296486 A1* | 12/2008 | Blanksby et al. | ............ 250/282 |
| 2009/0173877 A1* | 7/2009 | Bateman et al. | ............ 250/282 |

* cited by examiner

*Primary Examiner* — Nicole Ippolito
*Assistant Examiner* — Hanway Chang
(74) *Attorney, Agent, or Firm* — McCarter & English, LLP; Deborah M. Vernon; Michael J. DeGrazia

(57) ABSTRACT

The present disclosure relates, in part, to MS apparatus, methods, and/or software, having improved selectivity, sensitivity, specificity, resolution, mass accuracy and dynamic range over conventional MS technologies. In particular, the technology relates to apparatus, methods, and/or software wherein a combination of in-source fragmentation, ion mobility separation, and/or time-aligned parallel (TAP) sample ion fragmentations are utilized in mass spectrometry for the analysis of samples.

17 Claims, 9 Drawing Sheets

METHODS AND APPARATUS FOR PERFORMING MASS SPECTROMETRY

RELATED APPLICATIONS

This application is a 35 U.S.C. §371 national stage filing of International Application No. PCT/US2013/044649, filed Jun. 7, 2013, claims the benefit of U.S. Provisional Application No. 61/656,647, filed Jun. 7, 2012, and U.S. Provisional Application No. 61/693,890, filed Aug. 28, 2012. The entire teachings of the above applications are incorporated herein by reference.

FIELD OF THE TECHNOLOGY

In general, the field of the technology of the present disclosure relates to apparatus, methods, and software for performing mass spectroscopy. In particular, the technology relates to the use of insource and/or metastable ions as precursor ions for increasing one or more of selectivity, sensitivity, specificity and dynamic range of obtained spectra using the apparatus, methods, and/or software in accordance with the present technology.

BACKGROUND

Mass spectrometry (MS) is an analytical technique that measures the mass-to-charge ratio of a charged molecule or molecule fragments formed from a sample. MS is used to analyze the mass, chemical composition, and/or chemical structure of a sample of interest. In general, MS includes three steps: ionizing a sample to form charged molecules or molecule fragments (i.e., ions); separating the ions according to their mass-to-charge ratio; and detecting the separated ions to form a mass-to-charge signal (i.e., spectra).

There are many different types of MS devices. For example, sector, time-of-flight, quadrupole, ion trap, Fourier transform ion cyclotron resonance, and tandem (two or more of the above combined in tandem or orthogonal) mass spectrometers are all different instruments that are considered to be MS devices. Each device has its own limitations with respect to the analysis and obtained spectra of samples. Certain characteristics of MS analysis include, e.g., mass accuracy, resolution, sensitivity, dynamic range, selectivity, and specificity etc.

MS data analysis is a complicated subject, in which the degree of accuracy of data interpretation on mass, chemical composition, and chemical structure is limited by one or more of the above analysis characteristics of the instruments and/or operational methods utilized. Typically, an ion mobility spectrometer is composed of an ionization source, a drift cell and an ion detector. Instruments of these types allow for separation and analysis of ions according to their mobility and mass-to-charge ratio (m/z) in a gas phase, which in turn adds one additional dimension of separation. This added dimension of separation is beneficial for the identification of molecules of interest. The challenging issue, however, has been to effectively discriminate and take advantage of downstream non-parent ions to improve the overall sensitivity, selectivity, specificity, and/or dynamic range of a sample.

One such method for improvement deals with, for example, enhancing the sensitivity and/or selectivity in Matrix-Assisted Laser Desorption/Ionization (MALDI) experiments for structural elucidation of samples. During a MALDI experiment, there are three types of ions formed: stable ions with insufficient excitation energy to dissociate before detection, e.g., precursor or parent ions; unstable ions with enough energy to dissociate before leaving the ionization source, and metastable ions with intermediate energy which decomposes in transit. Typically, in this experiment, a sample is ionized and the resulting ions are separated by their mass-to-charge ratios in an analyzer.

SUMMARY

The present disclosure relates, in part, to improved methods and apparatuses for discriminating and/or enhancing downstream non-parent ions to obtain additional information for molecular structure elucidation using MS technology.

Further, the present disclosure relates, in part, to MS apparatus, methods, and/or software, having improved selectivity, sensitivity, specificity, dynamic range, and/or mass accuracy over conventional MS technologies. In particular, the present technology relates to apparatus, methods, and/or software wherein a combination of in-source fragmentation, ion mobility separation, and time-aligned parallel (TAP) sample ion fragmentations are utilized in mass spectrometry for the analysis of samples. The methods described herein allow for an increased understanding of ion fragmentation pathways, increased analysis characteristics, and an increased ability to elucidate compound structures. Specifically, by eliciting first generation product ions (daughter ions) as the initial ions to which additional fragmentation processes occur, multiple ionic species can be simultaneously fragmented and subsequently time-aligned to furnish enhanced, and in some cases, new characteristic peaks of an unknown sample.

Exemplary embodiments of the present disclosure include, apparatuses and methods related to a MALDI High Definition Mass Spectrometer (HDMS) comprising a trap (e.g., a device comprising three traveling wave portions, wherein each portion comprises stacked-ring type ions guides, such as those commercially available from Waters Technologies Corporation, Milford, Mass., USA, and comprised in, e.g., the device branded as TriWave®), an ion mobility drift cell (e.g., such as those commercially available from Waters Technologies Corporation, also as comprised in, e.g., the device branded as TriWave®) and transfer (e.g., such as those commercially available from Waters Technologies Corporation, and comprised in, e.g., the device branded as TriWave®) for Time-Aligned Parallel (TAP) fragmentation experiment.

Also provided herein are apparatuses and methods for forming first generation (daughter), second generation (granddaughter), and third generation (great-granddaughter) product ions, such as, in a MALDI source, wherein the first generation produce ions are selected as precursor instead of intact molecular or parent ions.

Also, the present disclosure relates, in part, to a computer-implemented method for separating and analyzing ions using an energy source to ionize at least a portion of a sample into first generation product ions (e.g., daughter ions) having substantially maximum intensity; detecting for a presence of first generation product ions having a mass of interest via a detector; receiving, by a processor, data from the detector on the presence of the portion of the first generation product ions having a mass of interest; determining, by the processor, whether the first generation product ions are present at a predetermined intensity or greater, based on a target ion list stored in memory; upon determining that the first generation product ions are present at the predetermined intensity or greater, the ions of interest are then isolated by an ion selection device (e.g., a quadrupole) and adjusting, by the processor, control settings to a first fragmentation cell, such that at least a portion of the first generation product ions having a mass of interest are fragmented to produce second generation product ions (e.g., granddaughter ions); at least a portion of the second generation product ions are separated by mobility; and at least a portion of the mobility separated second generation product ions are fragmented to produce third generation product ions (e.g., great-granddaughter ions) and maintaining of the mobility separated second generation ions; and detecting, by an MS detector a series of mass spectra, wherein mass peaks are associated with a different mobility value of the second generation product ions.

It would be understood that the methods and apparatuses described herein can be interfaced with a computer system, or software assisted spectra interpretation device, such that the parameters and optimization conditions for method control and variance, such as the laser power for ion fragmentation, gas flow, ion mode, etc., can easily be manipulated via the computer system or software assisted spectra interpretation device.

Embodiments of the above methods can include one or more of the following features. The methods described herein can be used for analyzing any type of sample, such as, biologically-based compounds, e.g., proteins, glycans, and lipids, (e.g., phosphatidylcholines); and organic and inorganic small molecules. The analysis of samples, can comprise, for example, forming precursor ions (parent ions and/or molecular ions) from the sample and fragmenting at least a portion of the precursor ions at the source to produce first generation product ions having substantially maximal intensity (daughter ions). A portion of the first generation product ions can then be selected by a pre-determined m/z ratio to afford a portion of ions having a mass of interest. A portion of the mass-selected first generation product ions can then be fragmented to produce second generation product ions (granddaughter ions), in which a portion of the second generation product ions can then be separation by mobility. A portion of the mobility separated second generation product ions can then be fragmented to form third generation product ions (great-granddaughter ions), while maintaining a remaining portion of the mobility separated second generation ions. Both the third generation product ions and the remaining second generation product ions can be detected in a detector, such as, e.g., a Time of Flight (TOF) analyzer. From this, a series of mass spectra can be generated, wherein each mass spectrum can be associated with a different mobility value of the second generation product ions. Finally, the overall structural information of the sample of interest can be determined from the above mass spectra and methods. In one embodiment, the structural information obtained includes one or more of increased selectivity, sensitivity, dynamic range, specificity, resolution, and mass accuracy.

As further described herein, the first generation product ions can be formed in-source or within a collision cell, such as, e.g., a trap, and in one embodiment, a device comprising three traveling wave portions wherein each portion comprises stacked-ring type ion guides. Also, the amount of fragmentation of the first generation ions can vary.

As further described herein, the fragmentation amount of the second generation ions can also vary.

The methods described herein can also include allowing the third generation product ions to enter the detector substantially simultaneously with their associated mobility separated second generation product ions.

As further described herein, formation of the precursor ions can be achieved via routine MS ionization techniques, such as, for example, Electrospray ionization (ESI), Fast Atom Bombardment (FAB), Chemical Ionization (CI), Electron Impact (EI), Atmospheric Solids Analysis Ionization (ASAI), Atmospheric Pressure Photoionization (APPI), Desorption Electrospray Ionization (DESI), Atmospheric Pressure Vapor Source (APVS), or Matrix-Assisted Laser Desorption/Ionization (MALDI). Some embodiments further feature analysis enhancement associated with the ionization source. For example, in embodiments including a APVS, direct analysis in real time can be applied to enhance compound identification.

Embodiments of the present disclosure provide numerous advantages over prior art methods. For example, one or more of the methods and apparatuses described herein allow the users to choose between different precursor ions to control fragmentation processes, leading to a better understanding of the MS experiment fragmentation pathways. Another advantage provided by at least some of the embodiments of the present disclosure is the improvement of at least one of selectivity, sensitivity dynamic range, specificity, resolution, and mass accuracy. In turn, at least selectivity and sensitivity increase the ability to elucidate structural characteristics of molecular scaffolds of interest, e.g., elucidating the localization of fatty acyl double bond positions for lipids on tissue samples.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION

Exemplary embodiments relate to an MS apparatus comprising MALDI TAP experiments.

The aforementioned and following methods and apparatuses can be useful for any type of samples, which include, but not limited to, biological-based compounds such as proteins, peptides, glycans lipids, (e.g., phosphatidylcholines), and organic and inorganic small molecules. Also, it would be apparent that the methods and apparatuses described herein can be employed in both negative and positive ion modes.

Figure 1:
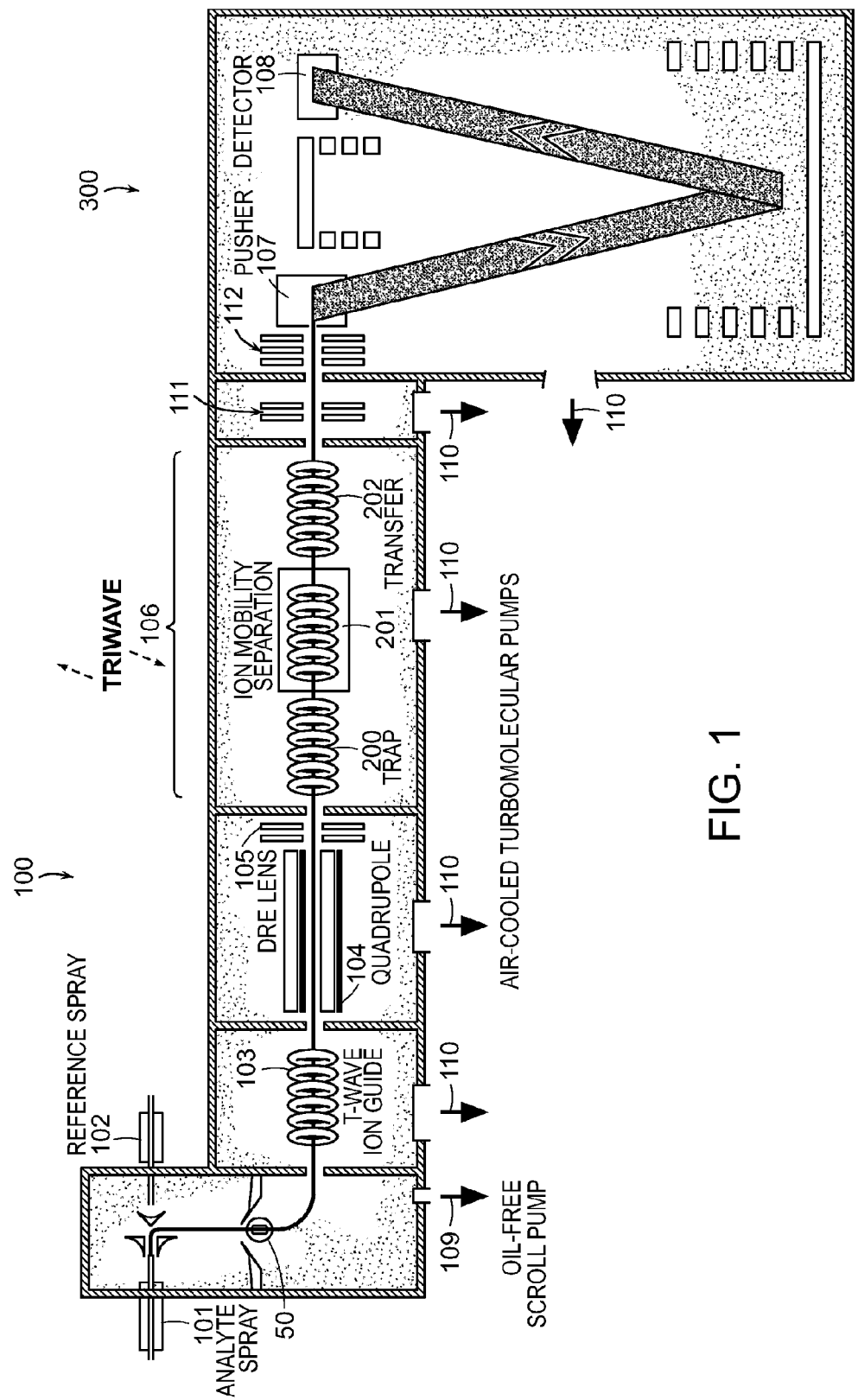
FIG. 1 is a schematic of a MALDI HDMS apparatus according to an exemplary embodiment of the present disclosure.

An example of a MS apparatus 100 according to the present disclosure is shown by FIG. 1. The periphery of the MS apparatus may contain an oil-free scroll pump port 109 and air-cooled turbomolecular pumps 110.

Ionization methods can include, ESI, FAB, CI, EI, ASAI, APPI, DESI, APVS or MALDI.

A sample mixture, comprising an analyte and carrier solvent, typically referred to as the precursor or parent ion, enters through port 101 in conjunction with a lockmass reference 102. The mixture then passes through ionization source 50, such as ESI, FAB, CI, EI, ASAI, APPI, DESI, APVS or MALDI, where the precursor or parent ions are initially ionized to form a plurality of first generation product ions (daughter ions). These ions then travel through ion guide 103 comprising three traveling waves (T-Waves) generated by an R.F. only stacked ring ion guide. This approach minimizes ions transit times, enables fast switching experiments, and virtually eliminates crosstalk before entry into quadrupole 104. This method is consistent with forming the first generation product ions in-source or within a collision cell. A similar method is described in U.S. Pat. No. 5,206,506, the contents of which are incorporated herein by reference.

During the above process, the amount of fragmentation of the first generation product ions in the source can be controlled by manipulating the laser energy. For example, for a lipid sample/analyte, such as 1-Palmitoyl-2-oleoyl-sn-glycero-3-phosphocholine, PC (16:0/18:1), when mixed with a matrix, such as 2,5 dihydrobenzoic acid (DHB) at a concentration of 1 µg/ml, the laser energy needed to dissociate the intact molecular ions is about 10 µJoules/pulse. Upon increasing laser energy, more intact molecular ions are dissociated. It would be apparent that different laser energy levels and ranges would depend on the sample and experimentation required to achieve the levels of fragmentation indicated above.

Upon separation of the first generation product ions from the sample, the ions are passed through a dry lens (105), and into an ion mobility device (106) comprising, in order, first, a trap region (200), second, an ion mobility separator region (201), and third, a transfer region (202). That is, within device (106), the ion mobility separator region (201) follows the trap region (200), and the transfer region (202) follows the ion mobility separator region (201) as shown in FIG. 1. Typically, further fragmentation of the first generation product ions entering device 106 can be induced in both the trap and transfer regions. Embodiments of the disclosure comprise inductions at approximately $10^{-3}$ mbar. Also, for ion mobility analysis, nitrogen or argon can be used as carrier gases at typical collision gas pressures, e.g., at a rate of approximately 0.5 mbar.

As discussed above, and explained in further detail below, the first generation product ions (daughter ions) enter the device (106) and are trapped within trap region (200). The first generation product ions are then fragmented in the trap to produce second generation product ions (granddaughter ions), which are then separated in the ion mobility separation region 201.

Upon mobility separation of the second generation product ions (granddaughter ions), these ions are then passed into the transfer region 202, where a certain amount of second generation product ions are further fragmented. Both the remaining (un-fragmented) separated second generation product ions and the newly formed third generation product ions (great-granddaughter ions) pass through a series of lenses (such as Einzel Lens 111 and Transfer Lenses 112) and flow through a TOF analyzer 300 comprising a pusher (107) and detector (108). The third generation product ions and the remaining separated second generation product ions enter the detector substantially simultaneously, i.e., at the same time or within reasonable instrumentation or operator error, and form the basis for a series of mass spectra for sample analysis where each mass spectrum is associated with a different mobility of the remaining second generation product ions.

Figure 2:
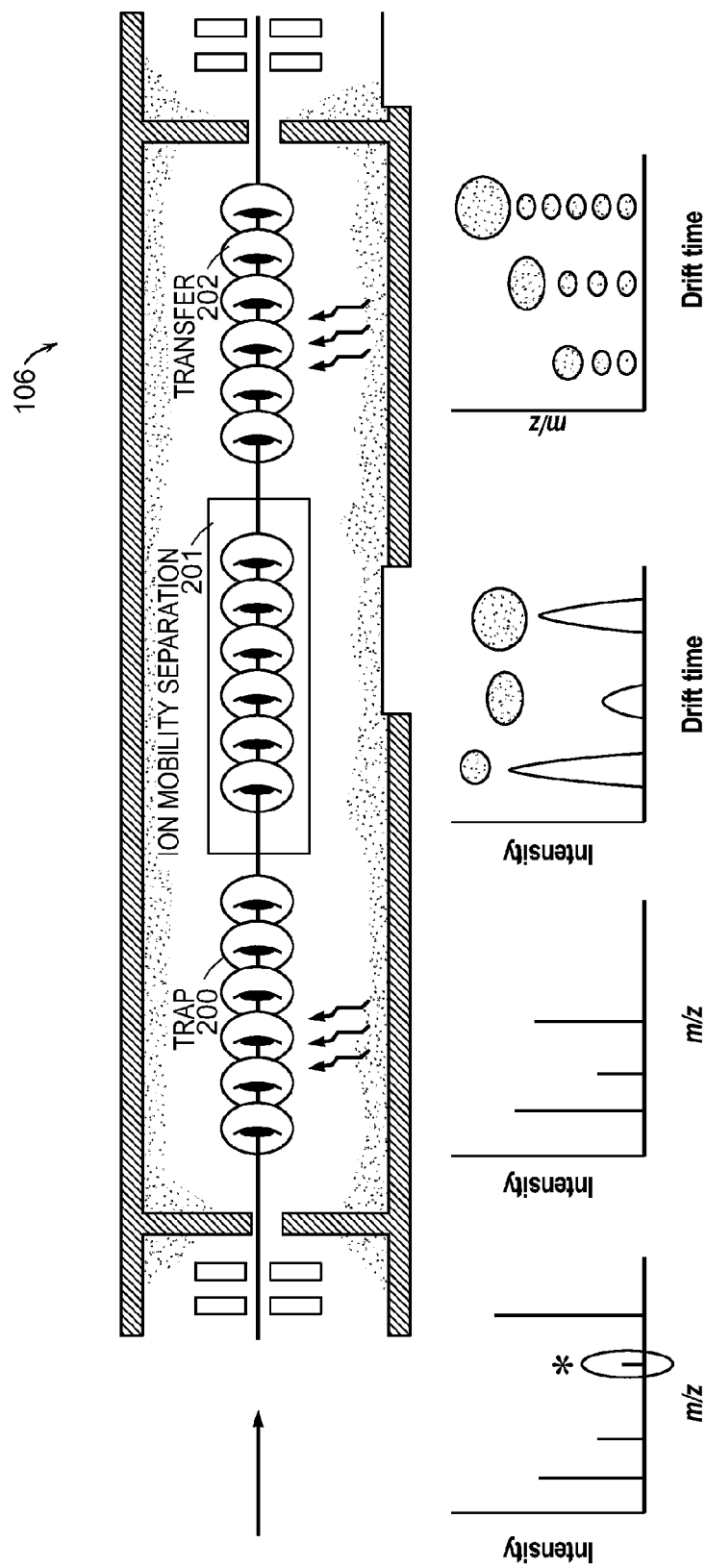
FIG. 2 is an example of an ion mobility device including a trap, a mobility cell, and a transfer apparatus used in a (time-aligned-parallel) TAP experiment according to an exemplary embodiment of the present disclosure.

FIG. 2 show an expanded version of the trap region, ion mobility region, and transfer region comprised in device 106. Following the methods described above, and illustrated by FIG. 2, prior the entry into device 106, the first generation product ions formed in the source (50) and isolated in various m/z ratios quadrupole 104 are fragmented in the trap 200 to form second generation product ions. The second generation product ions then pass through an ion mobility separator 201 and are subsequently shuttled to the transfer trap 202. The now time aligned second generation product ions and third generation product ions pass out of the device 106 and into the TOF analyzer 300.

Figure 3:
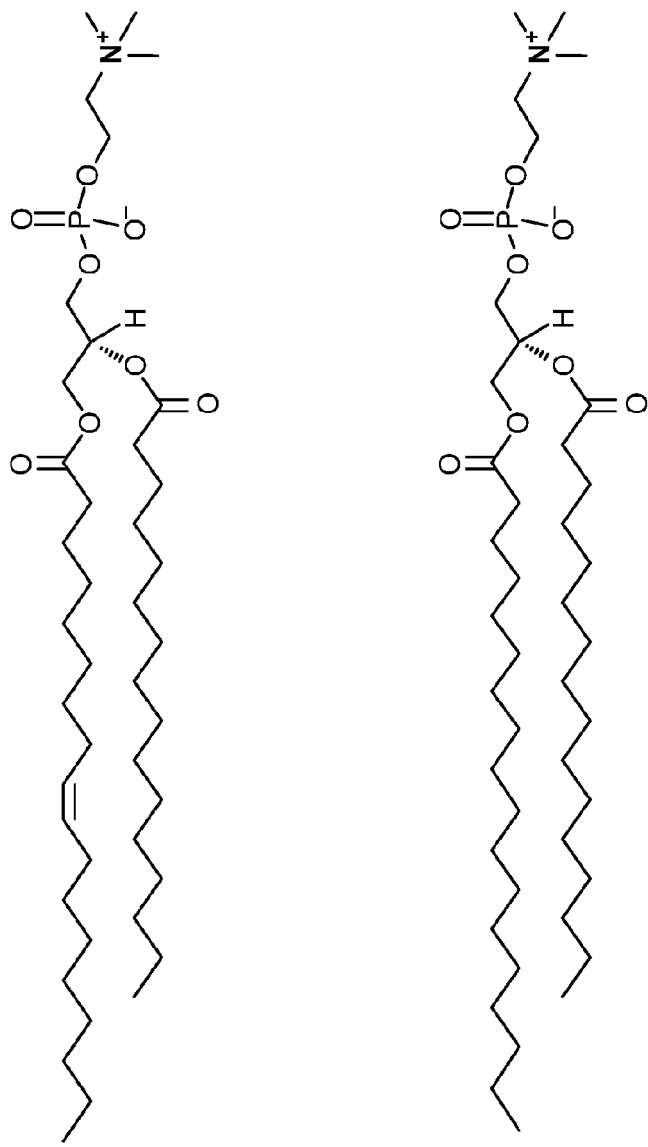
FIG. 3 shows the structures of certain phosphatidylcholines standards used in the exemplary methods described herein.

FIG. 3 shows the structures and molecular weights of the lipid standards PC (16:0/18:0) and PC (16:0/18:1) for reference in the following figures. In the description below, both PC (16:0/18:0) and PC (16:0/18:1) where dissolved in chloroform and diluted in isopropanol to make a solution of about 0.1 mg/mL. DHB matrix was then dissolved in isopropanol to make a solution of 25 mg/mL. 0.5 µL of the lipid standard solution was spotted on to MALDI target samples wells, air dried, and then 0.5 µL of the matrix solution was added on top.

Figure 4:
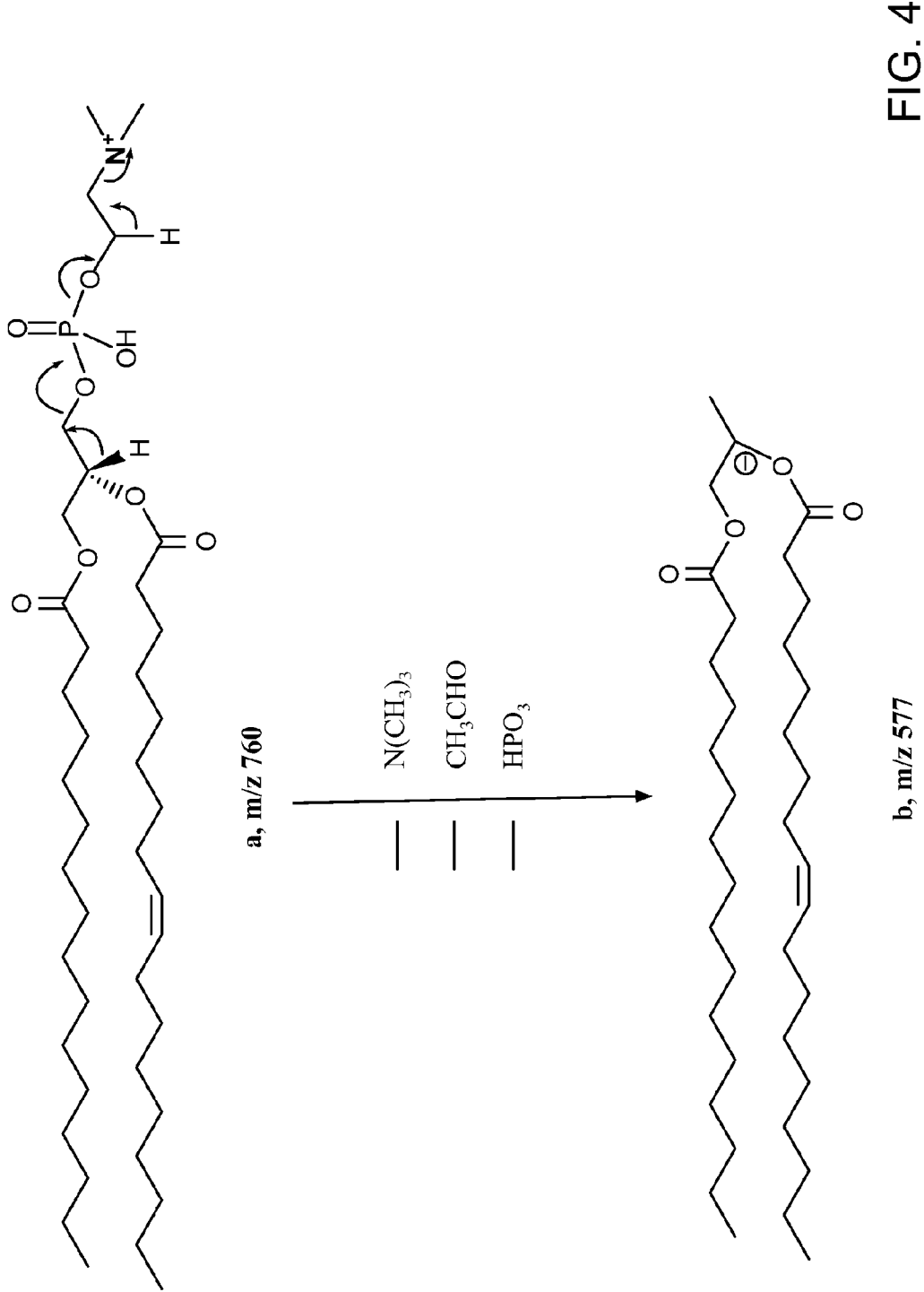
FIG. 4 shows the proposed mechanism for the formation of M-phosphorylcholine ion arising from the exemplary methods described herein.

MALDI was operated in positive Time-of-Flight or High Definition MS ion mobility mode. For both PCs, higher laser energy (about 95 µJoules/pulse) were used to generate in source fragmentations from the loss of the phosphate head group (approximately 183) of the parent ion at m/z 760.5. First generation product ions at a m/z of 577 and 579 were used as the precursors ions for further fragmentation and analysis. The generation of the m/z 577 ion is postulated in FIG. 4 for PC (16:0/18:1) (9Z). See, e.g, previous studies by Castro-Perez, J. J. Am. Soc. Mass Spectrom, 22; 8; 2011, the contents of which are incorporated herein by reference.

Figure 5A:
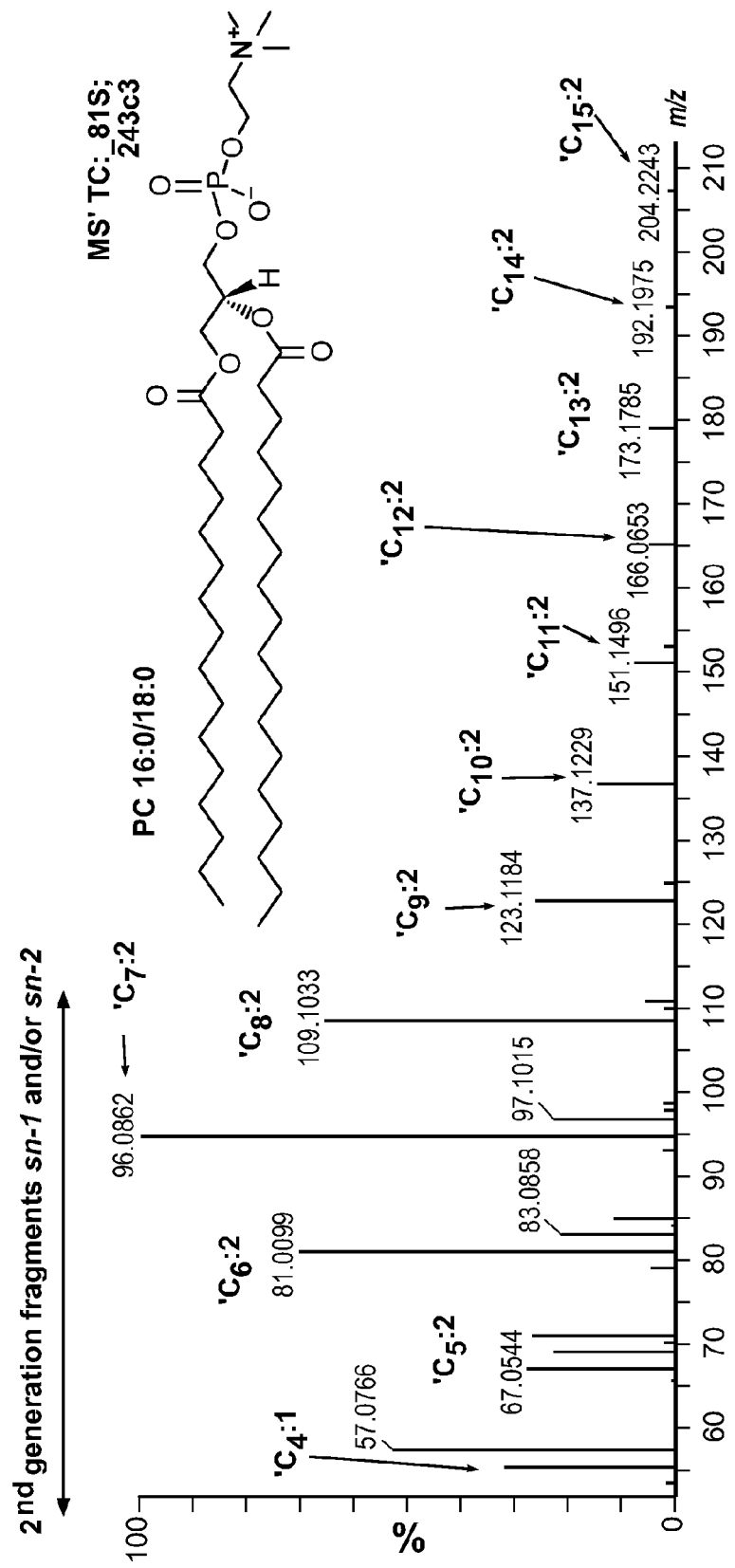
FIGS. 5A and 5B represent fragmentation peaks of certain phosphatidylcholine standards used in the exemplary methods described herein.
Figure 5B:
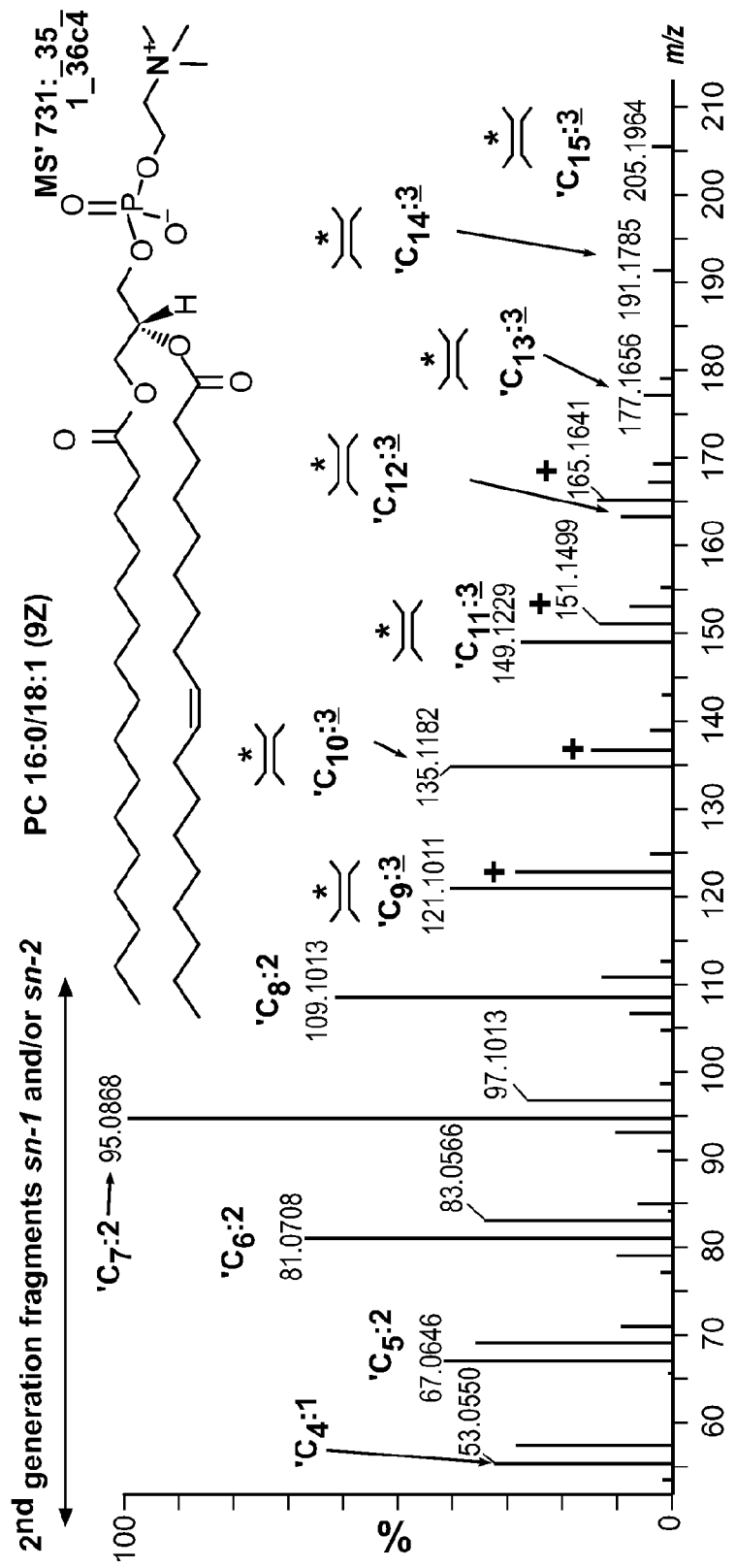

It should be noted that the most abundant hydrocarbon fragment ions as observed in FIG. 5a also have two double bonds, indicating that the dehydrated acylium ions $C16H29^+$ and $C_{18}H_{33}^+$ are the key precursor ions for their formation (note that FIG. 5a refers to PC 16:0/18:0 having two saturated fatty acid groups). In comparing the $C_5H_7^+$ ion to its higher homologues, it can be seen that from $C_9$ containing ions onwards the hydrocarbon fragments not only possess two double bonds, but also three double bonds. The latter must originate from the FA 18:1(9Z) chain, and the fact that $C_9H_{13}^+$ is the first ion having three double bonds is in perfect agreement with the double bond at position 9 of the fatty acid chain sn-2 (FIG. 5b), irrespective of the pathway of its formation.

Figure 6:
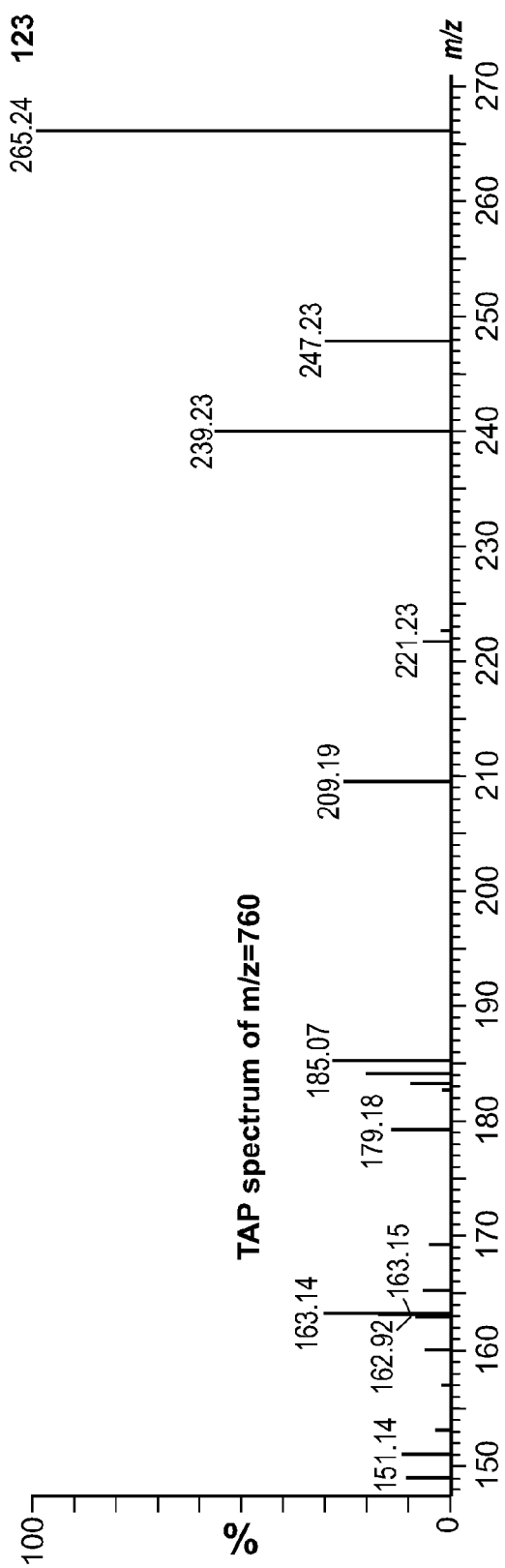
FIG. 6 shows comparative spectra of certain phosphatidylcholines extracted from conventional methods and those as described in the embodiments herein.
Figure 6:
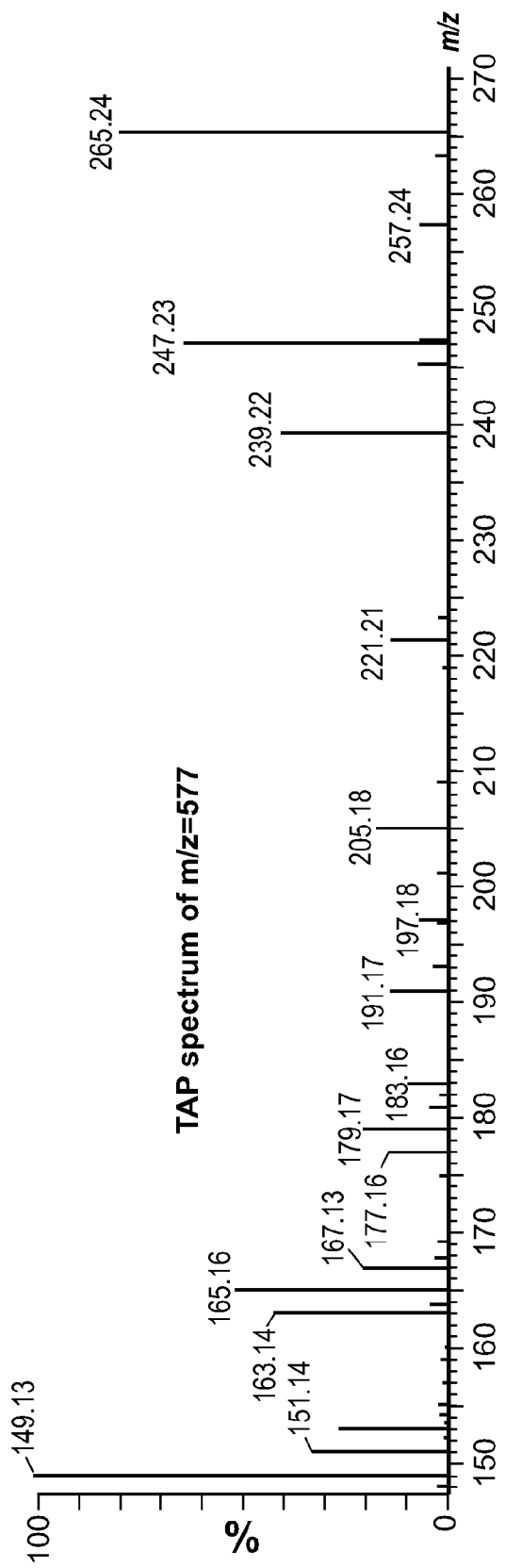

In line with the above, FIG. 6 shows comparative spectra of the lipid standard PC (16:0/18:0) obtained between conventional TOF analysis (top spectra) to that of the device (106)/TAP experiment and/or apparatuses described herein. Conventional methods would employ analysis of the intact molecular ion peak at a standard m/z ratio of 760. In contrast, the present method allows for fragmentation of the molecular ion peak in the initial trap (200) of device (106), wherein the resulting spectra is a combination of time-aligned fragments of the fragmented molecular ions (second fragmentation product ions) and third generation product ions. Thus, the third generation product ions correlate back to the second generation product ions, as opposed to the molecular parent ions, to form the bottom spectra of FIG. 6. The spectra obtained from the methods described herein is not only cleaner, which is important for determining double bond location in subsequent experiments, but also provides much higher intensity and shows fragmentation peaks that are absent from conventional methods. See, e.g., the m/z peaks at 191.17 and 197.18 of the bottom spectra.

Figure 7:
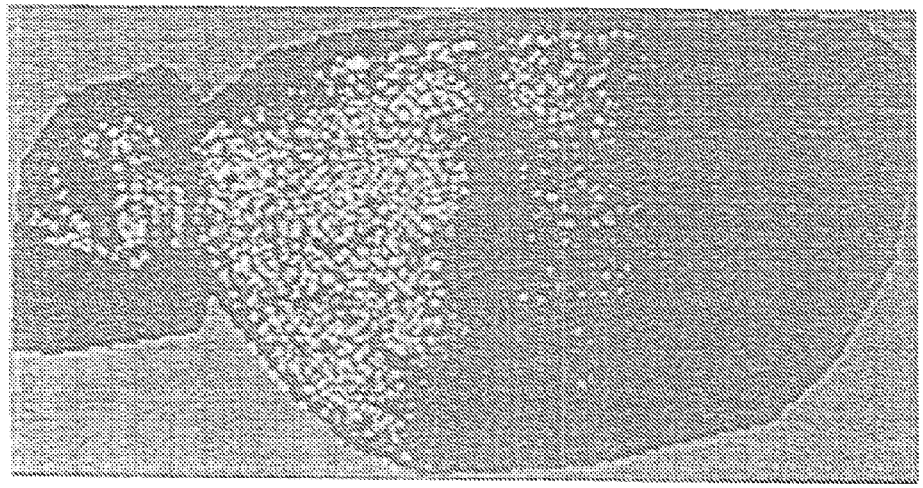
FIG. 7 represents an exemplary comparison of lipid biomarker MALDI image localization and distribution in brain tissues of rats using High Definition Imaging (HDI).
Figure 7:
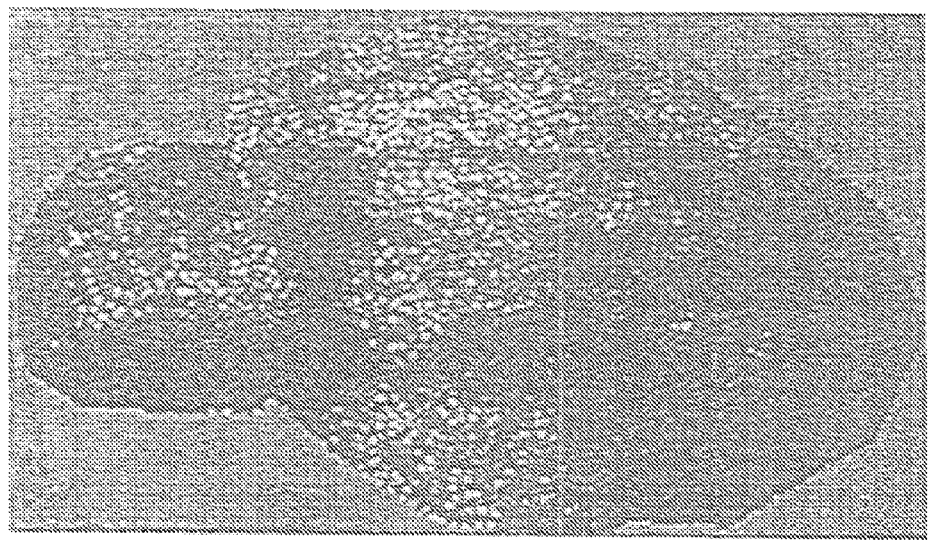

To further deduce the advantages of the methods and apparatuses described herein, FIG. 7 shows a pair of MALDI images taken from rat brain tissues where the rats were fed with different diets. The images shown were generated from the PC 16:0/18:1 lipid in the tissue of the rats. As shown, the distribution of the lipid molecules in the tissues are different, which indicates the improvement of sensitivity, selectivity, specificity, and dynamic range when using methods described herein.

It would be understood by the foregoing, that the present methods could also be employed for multi-step characterization of subsequent ion fragmentation and is not limited to $1^{st}$ through $3^{rd}$ generation fragmentation ions. For example, a contemplated method for multiple fragmentations and analysis may involve, a method of analyzing a sample, the method comprising: treating the sample with energy to convert at least a portion of the sample into a plurality of ions formed from precursor ions (e.g., parent ions); isolating at least a portion of the plurality of ions, defining an $\eta$ ion sample, where $\eta$ is an integer greater than 0; fragmenting at least a portion of the $\eta$ ion sample to produce a $\eta+1$ plurality of ions; isolating at least a portion of the $\eta+1$ plurality of ions, defining an $\eta+2$ ion sample; separating at least a portion of the $\eta+2$ ion sample by mobility, forming a mobility drift time aligned mass spectrum of at least a portion of the $\eta+2$ ion sample; fragmenting at least a portion of the $\eta+2$ ion sample to produce an $\eta+3$ plurality of ions, such that at least a portion of the $\eta+3$ plurality of ions are aligned against the drift time-aligned mass spectrum of the $\eta+2$ ion sample; and detecting at least a portion of the $\eta+3$ plurality of ions.

It would also be understood by the foregoing that the present apparatuses described herein could be interfaced with a computer system and/or the present methods could be controlled by the computer system. For example, a computer system including one more processors can be interfaced with MS system 100 such that the ionization source 50 can be monitored and/or controlled by the computer system. In an embodiment, the computer system includes data stored in look up tables regarding energy requirements and/or ionization energy values of first generation product ions of numerous different samples. An operator of the MS system 100 with attached computer system, in one embodiment, would enter information about the sample to be analyzed to the computer system. The computer system utilizing data contained in its look up tables would then control the ionization source 50 to produce the first generation product ions. Upon detection of the presence of desired first generation product ions, the computer system could then operate the MS system to implement the methods described herein. In the event that the desired first generation product ions are not detected, the computer system could display that information to the user.

For example, an embodiment of the present disclosure provides a computer-implemented method for separating and analyzing ions using an energy source to ionize at least a portion of a sample into first generation product ions (e.g., daughter ions) having substantially maximum intensity; detecting for a presence of first generation product ions having a mass of interest via a detector; receiving, by a processor, data from the detector on the presence of the portion of the first generation product ions having a mass of interest; determining, by the processor, whether the first generation product ions are present at a predetermined intensity or greater, based on a target ion list stored in memory; upon determining that the first generation product ions are present at the predetermined intensity or greater, adjusting, by the processor, control settings to a first fragmentation cell (e.g., device 106), such that at least a portion of the first generation product ions having a mass of interest are fragmented to produce second generation product ions (e.g., granddaughter ions); at least a portion of the second generation product ions are separated by mobility; and at least a portion of the mobility separated second generation product ions are fragmented to produce third generation product ions (e.g., great-granddaughter ions) and maintaining of the mobility separated second generation ions; and detecting, by an MS detector a series of mass spectra, wherein mass peaks are associated with a different mobility value of the second generation product ions.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other functions and advantages are also within the scope of the invention.

What is claimed is:

1. A method of forming structural information of a sample comprising lipids using mass spectrometry, comprising:
   optimizing ionization source conditions to produce first generation product ions at the source having substantially maximum intensity;
   mass selecting, from the first generation product ions, ions having a mass of interest;
   fragmenting at least a portion of the mass-selected first generation product ions to produce second generation product ions;
   separating at least a portion of the second generation product ions by mobility;
   fragmenting a portion of the mobility separated second generation product ions to produce third generation product ions, and maintaining a remaining portion of the mobility separated second generation ions, wherein the third generation product ions are time aligned with the second generation product ions;
   detecting, by a detector, the third generation product ions and the remaining portion of the mobility separated second generation product ions to form a series of mass spectra comprising time aligned fragmentation patterns, each mass spectrum being associated with a different mobility value of the second generation product ions; and determining the position of a fatty acyl double bond in the lipid from the time aligned fragmentation patterns.

2. The method of claim 1, wherein the ionization source is selected from Electrospray Ionization, Matrix Assisted Laser Desorption/Ionization, Chemical Ionization, Atmospheric Solids Analysis Ionization, Atmospheric Pressure Vapor Source, Desorption Electrospray Ionization, and Atmospheric Pressure Photoionization.

3. The method of claim 2, wherein the ionization source is Matrix Assisted Laser Desorption/Ionization.

4. The method of claim 2, wherein the ionization source is Electrospray Ionization.

5. The method of claim 1, wherein the fragmentation is performed in the source.

6. The method of claim 1, wherein the fragmentation and the mobility separation is performed in a device comprising three traveling wave portions, wherein each portion comprises stacked-ring type ions guides.

7. The method of claim 1, wherein the lipids comprise phosphatidylcholines.

8. A method of forming structural information of a sample comprising lipids using mass spectrometry, comprising:
    optimizing ionization source conditions to produce first generation product ions at the source having substantially maximum intensity;
    isolating the first generation product ions in the quadrupole;
    fragmenting the first generation ions in a device comprising three traveling wave portions, wherein each portion comprises stacked-ring type ions guides, to produce second and third generation product ions, wherein the third generation product ions are time aligned with the second generation product ions;
    detecting, by a detector, at least a portion of the third generation product ions to form a series of mass spectra comprising time aligned fragmentation patterns, wherein the structural information comprises one or more of increased selectivity, sensitivity, dynamic range, specificity, resolution, and mass accuracy; and
    determining the position of a fatty acyl double bond in the lipid from the time aligned fragmentation patterns.

9. The method of claim 8, further comprising one or more of the steps of mass selecting, from the first generation product ions, ions having a mass of interest;
    fragmenting at least a portion of the mass-selected first generation product ions to produce second generation product ions;
    separating at least a portion of the second generation product ions by mobility; and
    fragmenting a portion of the mobility separated second generation product ions to produce third generation product ions, and maintaining a remaining portion of the mobility separated second generation ions.

10. The method of claim 9, wherein the third generation product ions are time aligned with the second generation product ions.

11. The method of claim 8, wherein the ionization source is selected from Electrospray Ionization, Matrix Assisted Laser Desorption/Ionization, Chemical Ionization, Atmospheric Solids Analysis Ionization, Atmospheric Pressure Vapor Source, Desorption Electrospray Ionization, and Atmospheric Pressure Photoionization.

12. The method of claim 11, wherein the ionization source is Matrix Assisted Laser Desorption/Ionization.

13. The method of claim 11, wherein the ionization source is Electrospray Ionization.

14. The method of claim 8, wherein the lipids comprise phosphatidylcholines.

15. A method of forming structural information of a sample comprising lipids using mass spectrometry, comprising:
    passing the sample thorough a Matrix Assisted Laser Desorption/Ionization (MALDI) source to produce first generation product ions at the source having substantially maximum intensity;
    isolating the first generation product ions in a quadrupole;
    fragmenting the first generation ions in a device comprising three traveling wave portions, wherein each portion comprises stacked-ring type ions guides, to produce second and third generation product ions;
    detecting, by a detector, at least a portion of the third generation product ions to form a series of mass spectra.

16. The method of claim 15, further comprising one or more of the steps of mass selecting, from the first generation product ions, ions having a mass of interest;
    fragmenting at least a portion of the mass-selected first generation product ions to produce second generation product ions;
    separating at least a portion of the second generation product ions by mobility; and
    fragmenting a portion of the mobility separated second generation product ions to produce third generation product ions, and maintaining a remaining portion of the mobility separated second generation ions.

17. The method of claim 16, wherein the third generation product ions are time aligned with the second generation product ions.

* * * * *